United States Patent [19]

Hung

[11] Patent Number: 5,672,806
[45] Date of Patent: Sep. 30, 1997

[54] METHOD AND APPARATUS FOR CALIBRATING A GAS DETECTOR SENSOR

[75] Inventor: Patrick Hung, Richmond Hill, Canada

[73] Assignee: Patrick Plastics Inc., Weston, Canada

[21] Appl. No.: 332,030

[22] Filed: Oct. 31, 1994

[51] Int. Cl.[6] ..................................... G01N 1/00
[52] U.S. Cl. ..................................... 73/1 G
[58] Field of Search ............... 73/1 G, 4 R, 4 V, 73/1 D

[56] References Cited

U.S. PATENT DOCUMENTS

| | | |
|---|---|---|
| 4,150,366 | 4/1979 | Price . |
| 4,788,620 | 11/1988 | Scott . |
| 4,914,424 | 4/1990 | Hirao et al. ............. 73/1 G |
| 5,320,733 | 6/1994 | Bohm . |

Primary Examiner—Robert Raevis
Attorney, Agent, or Firm—Bereskin & Parr

[57] ABSTRACT

An improved method and apparatus for calibrating a gas sensor which exhibits a change in electrical characteristics in response to exposure to a gas. The apparatus comprises a resistor array and a chart. The chart comprises a list of predetermined resistor combinations corresponding to a range of output levels for the sensor. The resistor array is coupled to the output of the sensor. When exposed to a gas, the sensor exhibits a change in conductivity producing an output which generates an output signal with the resistor array. The level of the output signal is measured. The measured level is then compared to predetermined values on the chart which also lists the appropriate resistor combination for each value or range of values. The resistor combination is then set as indicated by the chart.

3 Claims, 6 Drawing Sheets

EQUIVALENT CIRCUIT
DURING CALIBRATION
PERIOD.

EQUIVALENT CIRCUIT
OF CALIBRATED SENSOR.

CALIBRATION VOLTAGE (Vc) VERSUS MATCHING RESISTANCE (R₁)

| Vc | $R_1$ | OPERATION |
|---|---|---|
| 2.1 V OR ABOVE | 5.8 k | NIL |
| 1.9 V OR ABOVE | 6.9 k | CUT R1 |
| 1.8 V OR ABOVE | 7.8 k | CUT R2 |
| 1.5 V OR ABOVE | 10 k | CUT R1 AND R2 |
| 1.2 V OR ABOVE | 13.7 k | CUT R3 |
| 0.8 V OR ABOVE | 22 k | CUT R1 AND R3 |
| 0.5 V OR ABOVE | 36 k | CUT R2 AND R3 |

LOOK-UP TABLE FOR PRODUCTION OPERATION

FIG. 8

METHOD AND APPARATUS FOR CALIBRATING A GAS DETECTOR SENSOR

FIELD OF THE INVENTION

This invention relates to gas detectors. More particularly, it relates to a method and apparatus for calibrating a sensor for use in a detector for gases.

BACKGROUND OF THE INVENTION

With the advent of stringent government standards and regulations, carbon monoxide detectors have become mandatory in many cities, such as Chicago. Other cities and states may follow suit requiring such detectors in residences.

Two types of sensors are commercially available: chemical enzyme and solid state. The enzyme-based sensor is also known as "jell cell" technology. While a jell cell sensor can effectively sense carbon monoxide, the operating life is relatively short, typically two years. Furthermore, the, jell cell sensor is vulnerable to substances normally found in a residential environment, e.g. household chemicals such as detergent and alcohol. Exposure to such substances can further reduce the operating life.

For these reasons, the solid-state type sensor is preferred. A solid state sensor, such as the Taguchi sensor available from Figaro Engineering Inc. and subject of U.S. Pat. No. 3,676,820, utilizes a tin dioxide compound which exhibits characteristic electrical properties when exposed to carbon monoxide. In the Taguchi sensor, the electrical conductivity of the tin oxide element increases when exposed to carbon monoxide. The change in conductivity is detected by an electronic circuit. To provide optimum operation, the tin oxide element is first heated to purge or burn off any residue which may have contaminated the surface of the element. The element is then allowed to cool down to a predetermined temperature which is optimum for sensing carbon monoxide. The sensor includes heaters which are used to heat up the sensor to 400° C. in order to purge nuisance gases which may collect on the surface and then the sensor is allowed to cool down to 100° C. which provides an interval for accurate sensitivity measurement. The Taguchi sensor is designed with the 400° C. purge heating and 100° C. sensing heating cycles lasting sixty seconds and ninety seconds respectively. Accordingly, the total time is two and a half minutes to complete one measurement cycle.

The Taguchi sensor is disclosed in U.S. Pat. No. 3,676,820. When compared to the chemical enzyme sensor, the Taguchi sensor has an operating life which is much longer and also the performance is much more robust with an operating life of up to five years in a residential application.

A gas detector incorporating a sensor of the Taguchi variety has been patented by Levine in Canadian Patent No. 1,017,968. The gas detector according to Levine comprises an apparatus having a heater oscillator for alternately heating and cooling the sensor to produce the purge heating cycle and the sensing cycle. The heater oscillator is intermittently turned on and off by a timing generator and the resistance of the sensor is measured by passing a current through it. According to Levine, the timing generator also controls the times of sampling, and a hold circuit is used to hold the sampled signal and convert them to a continuous signal. A threshold circuit senses when the continuous signal achieves a certain predetermined level, for example a level at which the concentration of carbon monoxide becomes dangerous and activates an alarm. The sensitivity of the detector to a particular gas, e.g. carbon monoxide or methane, is determined by calibrating the sensor using a potentiometer in series with the conductance of the sensor.

While the solid state type sensors can provide good field performance, it is still necessary to calibrate the sensitivity of each sensor, and the calibration must occur over the operating cycle. Due to the heating and cooling requirements as described above, e.g. the purge and cooling cycles, an operator is constrained by the two and a half minute cycle time. In known sensors, a circuit is included for sensitivity measurement which comprises the potentiometer in series with the sensor conductance. The potentiometer is adjusted manually in a real gas environment, for example a gas chamber, to a level which is considered to be an alarm level. The manual adjustment of the potentiometer must be performed during the two and a half minute interval. If the adjustment cannot be completed in time, then the sensor must be again cycled through the heat and cool down cycles, before calibration and adjustment can be performed. Furthermore the manual adjustment must also be performed with the sensor located in the gas chamber.

It will be appreciated that certain problems arise from this method and set-up. First, the entire measurement and adjustment procedure must be performed in synchronization with the two and a half minute cycle. Since the adjustment is made manually, calibration can be unreliable due to human error. Moreover, human error can also be introduced because the adjustment and calibration must be performed in the gas chamber.

Accordingly, there is a need for a method and apparatus for calibrating a solid state type gas sensor which minimizes the effect of human error and also provides an efficient technique for calibration of the sensor.

SUMMARY OF THE INVENTION

In a first aspect the present invention provides an apparatus for calibrating a gas sensor exhibiting a change in electrical characteristics in response to being exposed to a gas and having an output for a signal corresponding to said change in electrical characteristics, said apparatus comprising: (a) an array of resistors, said resistors being arranged to produce a predetermined resistance; (b) said array being coupled to the output of said sensor to produce an output signal corresponding to the electrical output response of the sensor; (c) said array including a test point for measuring the output signal; and (d) means for determining an arrangement of resistors in the array to provide a desired output response for the sensor based on the output signal measured at said test point.

In a second aspect, the present invention provides a method for calibrating a gas detector having a sensor exhibiting electrical characteristics in response to exposure to gas and having an array of fixed resistors for calibrating the electrical output characteristics of the sensor, said method comprising the steps of: (a) exposing the sensor to a predetermined concentration of a selected gas; (b) taking a measurement of the electrical output characteristic of the sensor; (c) comparing the measurement to a chart having a list of resistor combinations corresponding to electrical output characteristics of the sensor; and (d) implementing the resistor combination indicated by said chart for the desired electrical output characteristic of the sensor.

In a third aspect the present invention provides in a gas detector having a sensor for sensing a gas and a controller for producing an alarm when the gas level exceeds a predetermined threshold level, the sensor exhibiting electrical output characteristics in response to exposure to the gas and having an output, the improvement comprising: means for calibrating the electrical output characteristics of the sensor, said means for calibrating comprising an array of resistors arranged to produce a predetermined resistance, said array being coupled to the output of said sensor to produce an output signal corresponding to the electrical output response of the sensor, said array including a test point for measuring the output signal, and means for determining an arrangement of resistors in the array to provide a desired output response for the sensor based on the output signal measured at said test point.

The method and apparatus according to the present invention facilitates the calibration process because only one measurement needs to be taken and then the detector can be removed from the gas chamber. The resistor array is then set using the look-up table according to the present invention. It will be appreciated that the method and apparatus according to the present invention simplifies the calibration process and can save the amount of time required to calibrate a gas detector.

BRIEF DESCRIPTION OF THE DRAWINGS

For a better understanding of the present invention, and to show more clearly how it may be carried into effect, reference will now be made, by way of example, to the preferred embodiments of the present invention shown in the accompanying drawings in which:

FIG. 8 shows a LOOK-UP Table according to the present invention for selecting a resistance value for the calibration resistor array.

DETAILED DESCRIPTION OF THE PREFERRED EMBODIMENTS

Figure 1:
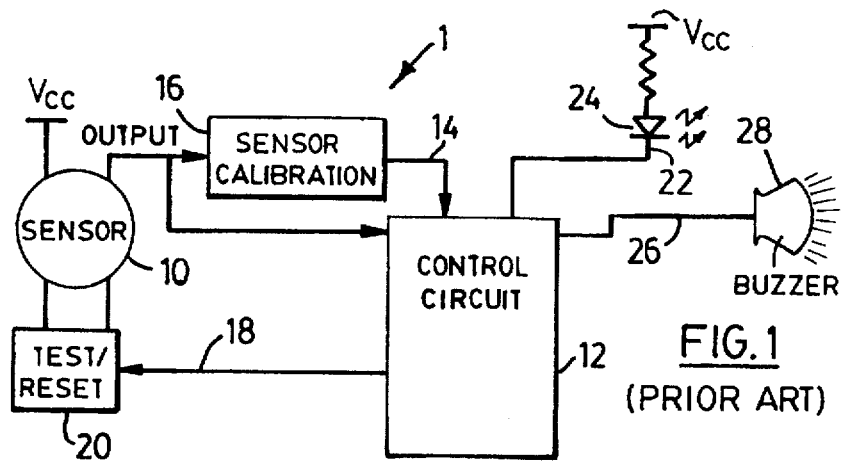
FIG. 1 shows in block diagram form a gas detector according to the prior art.

Reference is first made to FIG. 1 which shows a gas detector according to the prior art and indicated generally by reference 1. The gas detector 1 comprises a gas sensor 10 and a control circuit 12. The output of the sensor 10 is coupled to an input 14 of the control circuit 12 through a sensor calibrator 16. The sensor 10 is also coupled to a control output 18 from the control circuit 12 through a test/reset circuit 20. The control circuit 12 also includes one or more alarm outputs. As shown in FIG. 1, the alarm outputs comprise an output 22 coupled to a LED (Light Emitting Diode) 24 and an output 26 coupled to a buzzer 28. The control circuit 12 activates the LED 24 and the buzzer 26 if there is an alarm condition, i.e. detection of harmful gas levels. The control circuit 12 can be implemented in known manner, using a suitably programmed microcontroller, as is within the understanding of one skilled in the art, for example according to the teachings of Levine in Canadian Patent No. 1,017,698 and the disclosure of that patent is incorporated herein by this reference, or by using the FIC 5401 integrated circuit controller available from Figaro.

The gas sensor 10 may be of the above-mentioned Taguchi type employing an element 11 (FIG. 2) comprising a type IV or N-type metal oxide compound. The resistance of the element 11 decreases when it absorbs reducing gases, while the resistance increases when the element 11 absorbs oxygen. The sensitivity of the element 11 in the sensor 10 to gases depends on the temperature at which the element 11 is heated. For detection of carbon monoxide gas, the ideal temperature for the element 11 is 100° C. However, at this temperature and below, the sensitivity of the element 11 in the sensor 10 is easily influenced by water vapour and other substances in the ambient air. To overcome this problem, the sensor 10 is heated to a high temperature, typically 400° C. to purge the element 11, and then allowed to cool down to 100° C. for sensing the level of a gas, e.g. carbon monoxide, which may be present in the ambient air. The purge cycle burns the water vapour and other miscellaneous gases or contaminants from the surface of the element 11 and typically has a duration of 60 seconds. The purge period is followed by the cooling or sensing period during which time, the element 11 is highly sensitive to a selected gas, e.g. carbon monoxide. The sensing period has a duration of approximately 90 seconds. It will be appreciated that the sensitivity of the sensor 10 decreases as the element 11 becomes contaminated.

Figure 2:
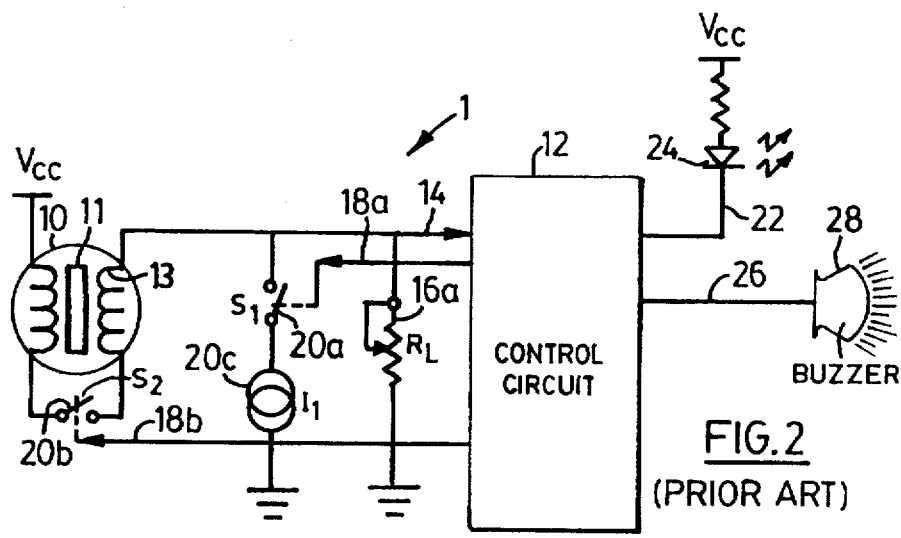
FIG. 2 shows in more detail the gas detector of FIG. 1 and a sensor calibration circuit according to the prior art.

Reference is next made to FIG. 2 which shows the gas detector 1 of FIG. 1 in more detail. As shown in FIG. 2, the test/reset circuit 20 comprises a first switch $S_1$ indicated by reference 20a, a second switch $S_2$ indicated by reference 20b and a current source $I_1$ indicated by reference 20c. The switches 20a, 20b can be implemented in known manner using a pair of transistors. The sensor calibrator 16 comprises a variable resistor or potentiometer indicated by reference 16a. The first switch $S_1$ is activated by the control circuit 12 through output line 18a and the second switch $S_2$ is activated by output line 18b. Controlled heating of the sensor 11 is accomplished by a heater coil indicated by reference 13 in FIG. 2. The heater coil 13 can be embedded in the sensor 11 material. The purge cycle is initiated by the control circuit 12 by closing switches 20a, 20b. With the switches closed 20a, 20b, a current flows through the heater coil 13 which heats the sensor 11 for the duration of the purge cycle, e.g. 60 seconds. The current which flows is set using the current source $I_1$ as will be understood by one skilled in the art. At the end of the purge cycle, the sensor element 11 is set to detect a gas, e.g. carbon monoxide, optimally and the switches 20a, 20b are opened. In response to contacting carbon monoxide, the resistance of the sensor 11 changes, i.e. the electrical conductivity rises, which produces a voltage level across the resistor 16a. The voltage level is read by the control circuit 12 on the input 14 and if the voltage exceeds a threshold level, the control circuit 12 activates an alarm, e.g. flashing the LED 24 and/or sounding the buzzer 28. In known manner, the sensor 10 is calibrated to provide optimum performance and sensitivity by adjusting the potentiometer 16a. Calibration of a prior art gas detectors 1 involves measuring the output of the sensor 10 at the end of the purge cycle and adjusting or "tweaking" the potentiometer 16a while the detector is still in a gas chamber 1 so that the sensor is exposed to carbon monoxide.

Figure 3:
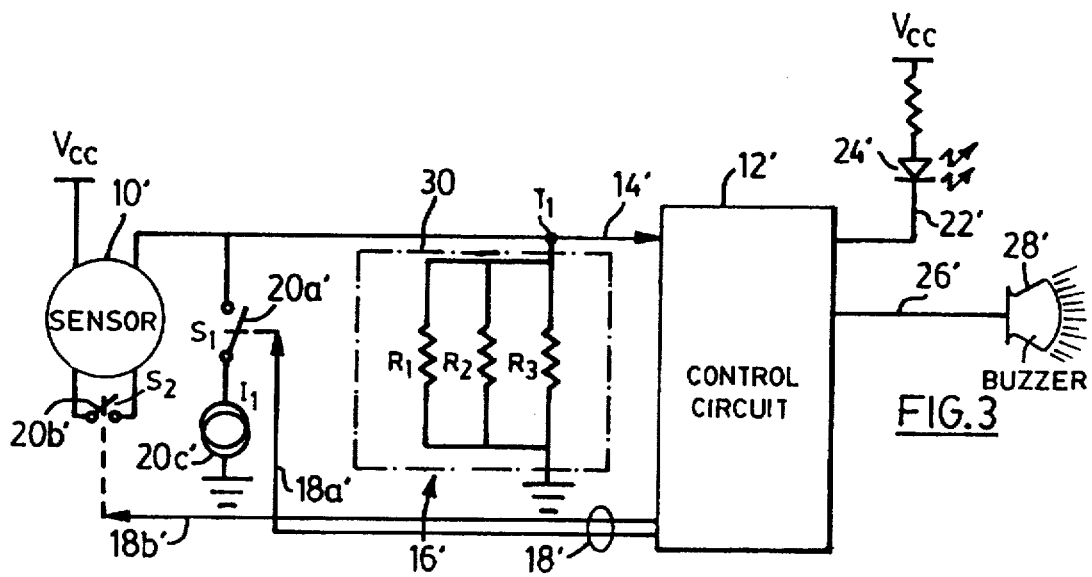
FIG. 3 shows the gas detector of FIG. 1 with a calibration circuit according to the present invention.

Reference is next made to FIG. 3 which shows a gas detector incorporating a sensor calibrator according to the present invention. The gas detector in FIG. 3 is indicated generally by reference 1' and like elements corresponding to FIG. 2 are indicated using primed reference numbers. For the gas detector 1' according to the present invention, the sensor calibrator 16' comprises an array of fixed resistors 30 as shown in FIG. 3. There is also a test node denoted by $T_1$ which is used to measure the output of the sensor 10' during calibration. The array 30 replaces the potentiometer 16a (FIG. 2) and is used in conjunction with a Look-Up Table 40 (FIG. 8) according to the present invention to accurately and quickly calibrate the sensor 10'.

Figure 9:
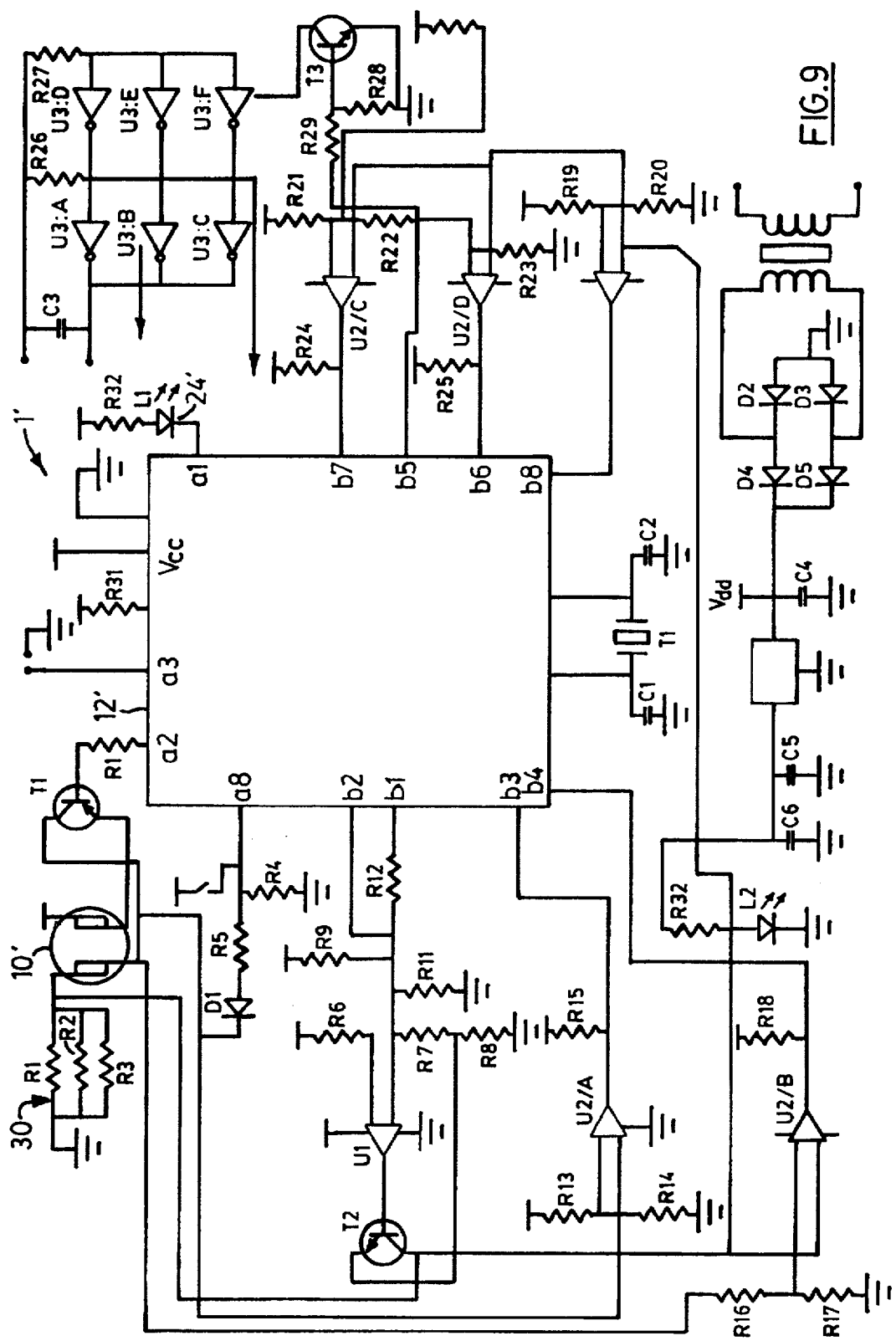
FIG. 9 is detailed schematic of an electronic circuit for a gas detector including the resistor array for calibration according to the present invention.

As shown in FIG. 3, the resistor array 30 comprises three resistors $R_1, R_2, R_3$. The resistors $R_1, R_2, R_3$ are mounted on the circuit board (not shown) when the detector 1' is assembled and prior to sensitivity calibration. The detailed circuit for the gas detector 1' according to the present invention is shown in FIG. 9, wherein the resistor array is indicated by reference 30 and the control circuit 12' is shown as U4 and comprises a microprocessor, such as the PIC16C5X microcontroller from Microchip Technology Inc., suitably programmed by one skilled in the art to provide the functionality described above.

Figure 4:
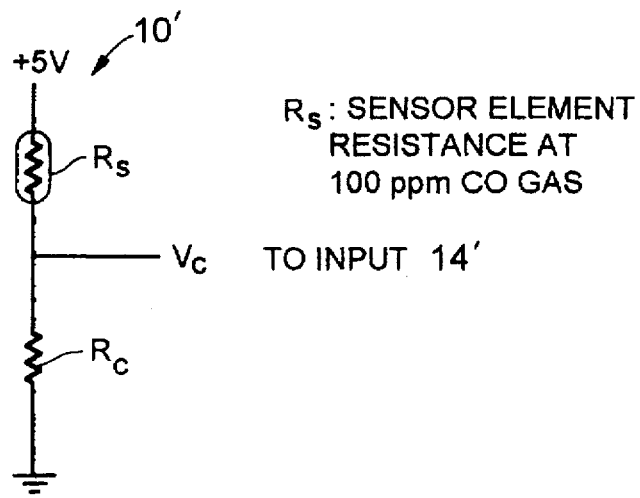
FIG. 4 shows an equivalent circuit for the sensor and resistor array according to present invention during the calibration period.

Reference is next made to FIG. 4 which shows an equivalent circuit for the sensor 10' during calibration. In FIG. 4, the resistance of the sensor 10' is represented by resistor $R_S$ and corresponds to the resistance of the sensor 10' at 100 ppm carbon-monoxide gas concentration, and the loading resistance during calibration is represented by resistor $R_C$. Voltage $V_C$ represents the output voltage of the sensor 10' which measured at test point $T_1$ (FIG. 3) by an operator during the calibration period. The output voltage $V_C$ of the sensor 10' is determined according to the following expression:

$$V_C = \frac{5 R_C}{R_S + R_C} \text{ Volts} \quad (1)$$

and therefore the resistance $R_S$ of the sensor 10' is given by the following expression:

$$R_S = \frac{R_C(5 - V_C)}{V_C} \text{ Ohms} \quad (2)$$

Therefore, according to the measured output voltage $V_C$, a value of the sensor resistance $R_S$ at 100 ppm can be calculated using equation (2).

Figure 5:
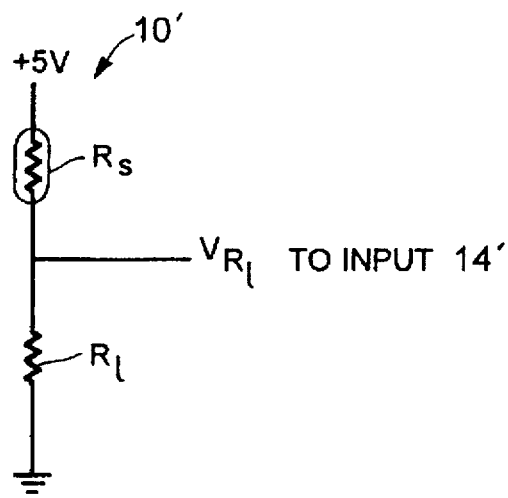
FIG. 5 shows an equivalent circuit for the calibrated sensor and resistor array according to the present invention.
Figure 6A:
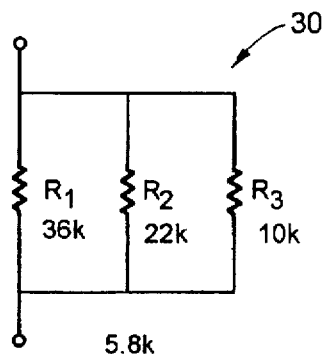
FIGS. 6(a) to 6(g) show in schematic form combinations of the calibration resistor array according to the present invention.
Figure 6B:
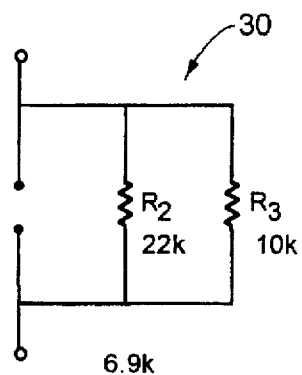
Figure 6C:
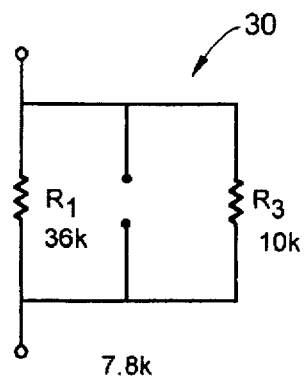
Figure 6D:
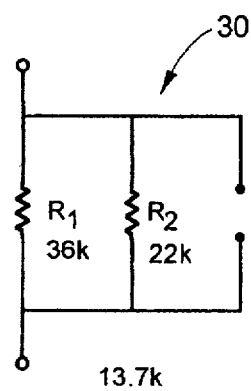
Figure 6E:
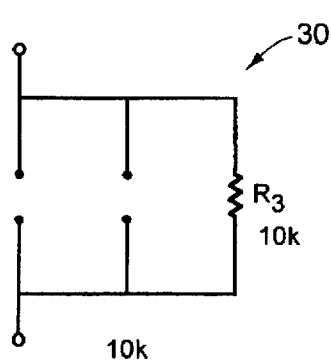
Figure 6F:
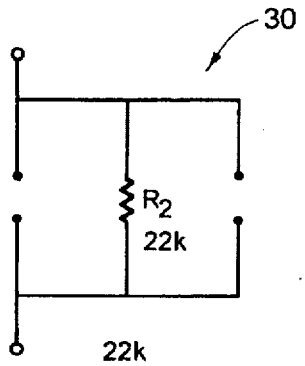
Figure 6G:
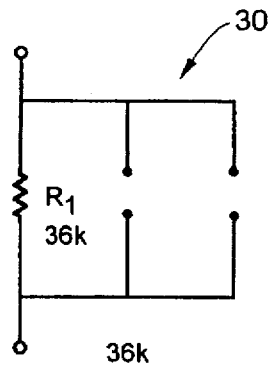

According to the invention to calibrate the sensitivity of the sensor 10', a value for the load resistance is set using the resistor array 30. In FIG. 5, the load resistance is represented by resistor $R_L$. The load resistance is selected so that the output voltage $V_{RL}$ of the sensor 10' is at or above the 100 ppm CO gas alarm threshold level voltage which is denoted by $V_{ref}$. According to the invention, the resistance value for $R_L$ is determined according to the following expression:

$$R_L(\min) = \frac{5 V_{ref} R_C}{V_C(5 - V_{ref})} - \frac{V_{ref} R_C}{5 - V_{ref}} \text{ Ohms} \quad (3)$$

Figure 7:
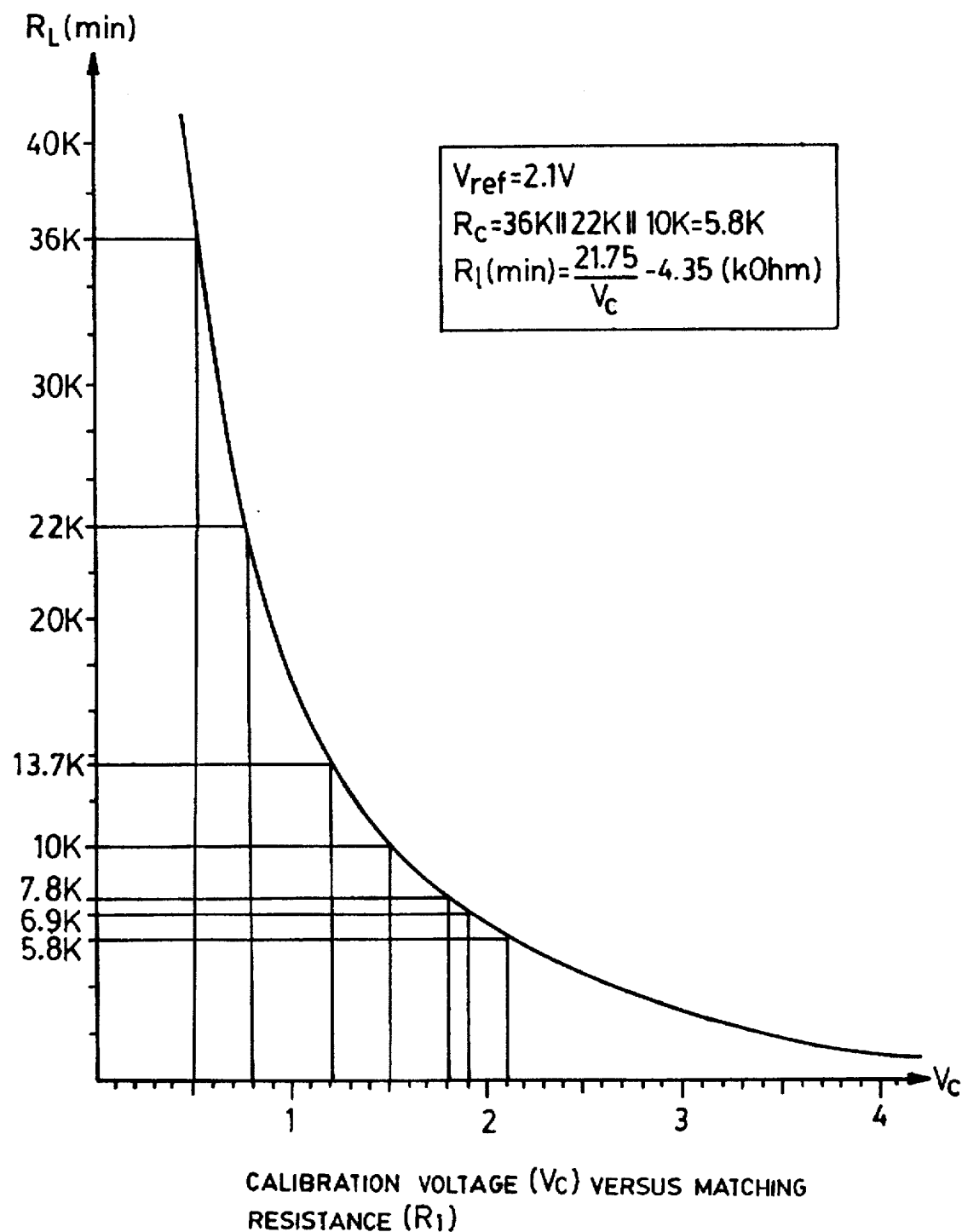
FIG. 7 shows in graphical form the relationship between the calibration voltage and the calibration resistance.

The relationship between the measured output voltage $V_C$ of the sensor 10' and a matched value for the load resistance $R_L$ is shown in FIG. 7. In FIG. 7, the voltage $V_C$ is the output voltage of the sensor 10' which is measured during calibration and the resistance $R_C$ corresponds to the parallel resistance value of the resistors $R_1, R_2, R_3$ comprising the resistor array 30, and resistance $R_{L(min)}$ represents the minimum resistance value of the loading resistor $R_L$ needed to ensure that the calibrated output voltage $V_{RL}$ of the sensor 10' reaches or is above the 100 ppm alarm threshold level. According to the invention, the resistors $R_1, R_2, R_3$ comprising the array 30 are combined to provide the minimum resistance value $R_L$ by selecting and removing (i.e. clipping) one or two of the resistors in the array 30 using a Look-Up table or chart 40 (FIG. 8) according to the present invention as will be described.

As shown in FIGS. 6(a) to 6(g), the resistor array 30 comprises the resistors $R_1, R_2, R_3$ which are selected to cover seven combinations of resistance as indicated. The seven combinations are selected to best match the typical conductance of the sensor 10' at 100 ppm of CO gas. For the Figaro TGS203 model gas sensor, the values for the resistors $R_1, R_2, R_3$ are selected to be 36K, 22K and 10K respectively. The three resisters $R_1, R_2, R_3$ comprising the calibration array are mounted in the circuit for the detector 1' during assembly and prior to sensitivity calibration.

According to the invention, at calibration, the voltage level, i.e. voltage $V_C$, at test point $T_1$ (FIG. 3) is measured with the sensor 10' exposed 100 ppm CO gas. The voltage $V_C$ measured at point $T_1$ is recorded and this level is used with a Look-Up Table 40 as shown in FIG. 8 to determine which resistor or resistors ($R_1$, $R_2$ or $R_3$) in the array 30 must be removed to best match the conductance characteristics of sensor 10' mounted in the detector 1'. For example, if the voltage $V_C$ measured at test point $T_1$ is 1.2 volts or above (and below 1.5 volts), then according to the Chart 40 shown in FIG. 8, resistor $R_3$ is cut from the array 30 (FIG. 3) in order to calibrate the sensor 10' for the proper output level.

Once the particular resistance value is determined from the Look-Up Table (FIG. 8), the operator or tester then simply cuts the unneeded resistor(s) ($R_1, R_2$ or $R_3$) from the array 30 and the detector 1' is tested for alarm activation. Following this operation, the detector 1' is calibrated and the calibration resistance is given by the remaining fixed resistors $R_1, R_2, R_3$. Because the load resistance $R_L$ is formed from a fixed resistor (or resistors), the resistance value is permanent and therefore more reliable than a variable potentiometer. Another feature of the calibration method according to the present invention is the elimination of the need to manually adjust the potentiometer 16a (FIG. 2) with the detector 1 in a gas chamber environment.

It will be appreciated that the resistor array 30 and Look-Up Table 40 (FIG. 8) according to the invention provide a simple and efficient method for calibrating a gas detector. The method according to the invention does not require the gas detector to be positioned inside a gas chamber for the operator to adjust or set the resistance value. Furthermore, the calibration resistor array 30 comprises fixed resistors $R_1, R_2, R_3$ (FIG. 3) which are more reliable than a variable potentiometer 16a (FIG. 2) while still providing a sufficient resistance range for calibrating the gas detector.

It will be evident to those skilled in the art that other embodiments of the invention fall within its spirit and scope as defined by the following claims.

I claim:

1. A method for calibrating a gas detector having a sensor exhibiting electrical characteristics in response to exposure to gas and having an array of fixed resistors for calibrating the electrical output characteristics of the sensor, said method comprising the steps of:

(a) exposing the sensor to a predetermined concentration of a selected gas;

(b) applying heat to the sensor;

(c) allowing the sensor to cool to an optimal sensing temperature;

(d) taking a measurement of the electrical output characteristic of the sensor while the sensor is at the optimal temperature;

(e) removing the sensor from the predetermined concentration of gas;

(f) comparing the measurement to a chart having a list of resistor combinations corresponding to electrical output characteristics of the sensor; and (g) implementing a resistor configuration within the array indicated by said chart to produce a desired electrical output characteristic of the sensor.

2. The method as claimed in claim 1, wherein the step of implementing the resistor combination comprises removing one or more selected resistors from a group resistors comprising the array of fixed resistors.

3. The method as claimed in claim 2, wherein said measurement comprises a voltage reading corresponding to the electrical output characteristic of the sensor.

* * * * *